(12) United States Patent
Roos et al.

(10) Patent No.: US 11,602,551 B2
(45) Date of Patent: Mar. 14, 2023

(54) USE OF INOSINE FOR THE TREATMENT OF T-REG DEFICIENCY

(71) Applicants: BioGaia AB, Stockholm (SE); Board of Regents of the University of Texas System, Austin, TX (US)

(72) Inventors: Stefan Roos, Uppsala (SE); Yuying Liu, Pearland, TX (US); Baokun He, Houston, TX (US); Jon Marc Rhoads, Houston, TX (US)

(73) Assignees: BioGaia AB, Stockholm (SE); Board of Regents of the University of Texas System, Austin, TX (US)

( * ) Notice: Subject to any disclaimer, the term of this patent is extended or adjusted under 35 U.S.C. 154(b) by 636 days.

(21) Appl. No.: 16/304,747

(22) PCT Filed: May 26, 2017

(86) PCT No.: PCT/EP2017/062800
§ 371 (c)(1),
(2) Date: Nov. 27, 2018

(87) PCT Pub. No.: WO2017/203048
PCT Pub. Date: Nov. 30, 2017

(65) Prior Publication Data
US 2021/0060098 A1 Mar. 4, 2021

Related U.S. Application Data

(60) Provisional application No. 62/342,508, filed on May 27, 2016.

(51) Int. Cl.
*A01N 63/00* (2020.01)
*A61K 35/747* (2015.01)
*A61P 37/04* (2006.01)

(52) U.S. Cl.
CPC ............ *A61K 35/747* (2013.01); *A61P 37/04* (2018.01)

(58) Field of Classification Search
None
See application file for complete search history.

(56) References Cited

FOREIGN PATENT DOCUMENTS

KR 100913405 B1 8/2009
KR 100913406 B1 8/2009

OTHER PUBLICATIONS

Matini et al. Journal of Allergy and Clinical Immunology, Elsevier, Amsterdam, NL, vol. 121, No. 2, 1031, Feb. 1, 2008 (Year: 2008).*
Ledesma-Amaro et al. Microbial Cell Factories (2015) (Year: 2015).*
Ledesma-Amaro et al. Microbial Cell Factories (2015) 14:58, i (Year: 2015).*
Yuying et al. Am J. physiol Gastrointest Liver Physiol. Mar. 15, 2012, 302(6). (Year: 2012).*
Database WPI Week 200962 Thomson Scientific, London, GB; AN 2009-N32996 XP002773575, & KR100 913 405 BI (Gwangju Inst Sci &Technology) Aug. 21, 2009 (Aug. 21, 2009) abstract.
Database WPI Week 200962 Thomson Scientific, London, GB; AN 2009-N32997 XP002773576, & KR 100 913 406 BI (Gwangju Inst Sci &Technology) Aug. 21, 2009 (Aug. 21, 2009) abstract.
He et al., "Resetting microbiota by Lactobacillus reuteri inhibits T reg deficiency-induced autoimmunity via adenosine A2A receptors", The Journal of Experimental Medicine, (214)(1), pp. 107-123 (2016).
International Depository Authority DSM 17938, dated Feb. 6, 2006; Viability Statement for DSM 17938 dated Feb. 6, 2006; 2 pages.
International Search Report and Written Opinion issued in International Application No. PCT/EP2017/062800, dated Sep. 28, 2017.
Karimi et al., "Lactobacillus reuteri-induced Regulatory T cells Protect against an Allergic Airway Response in Mice", American Journal of Respiratory and Critical Care Medicine, (179)(3), pp. 186-193 (2009).
Liu et al., "Oral Feeding Lactobacillus Reuteri DSM17938 Reduces Inflammation in Lungs of Treg-Deficient Scurfy Mice", URL:http://www.gastrojournal.org/article/S 0016-5085(15)31778-9/pdf; (2015) (abstract).

* cited by examiner

*Primary Examiner* — Jana A Hines
*Assistant Examiner* — Khatol S Shahnan Shah
(74) *Attorney, Agent, or Firm* — McNeill Baur PLLC

(57) ABSTRACT

The present invention provides the use of inosine in the treatment of a disease associated with Treg deficiency or Treg dysfunction, in particular immune dysregulation, polyendocrinopathy, enteropathy, X-linked syndrome (IPEX). In one embodiment of the invention, the inosine can be provided in the form of a bacterial strain that is capable of stimulating the production of inosine. Methods for stimulating the production of inosine in a subject using said strains are also provided, as are methods for the selection of a bacterial strain capable of stimulating inosine production in a subject.

12 Claims, 10 Drawing Sheets
Specification includes a Sequence Listing.

a  Early treatment of SF mice with *L. reuteri* (SFL)

b  Late treatment of SF mice with *L. reuteri* (SFL)

c  SF mice with inosine treatment (SFI)

Figure 5 cont.

| Super Pathway | Sub Pathway | Metabolite | SF/WT | SFL/SF |
|---|---|---|---|---|
| Amino Acid | Urea cycle; Arginine and Proline Metabolism | N-delta-acetylornithine | | R |
| | | N2,N5-diacetylornithine | | R |
| | | N-methylproline | | G |
| | Polyamine Metabolism | putrescine | LR | LR |
| | Glutathione Metabolism | ophthalmate | R | R |
| Carbohydrate | Pentose Metabolism | ribose | | R |
| Energy | TCA Cycle | malate | | LR |
| | | itaconate (methylenesuccinate) | LR | LR |
| | | tricarballylate | | G |
| | | caprylate (8:0) | | G |
| | Fatty Acid | 10-undecenoate (11:1n1) | R | LG |
| | | docosatrienoate (22:3n3) | R | G |
| | | 2-hydroxyglutarate | | LR |
| | | adipate | | LR |
| | | decanoylcarnitine | | G |
| | | 9,10-DiHOME | | G |
| Lipid | Phospholipid Metabolism | 1-palmitoyl-2-arachidonoyl-GPI (16:0/20:4)* | | LG |
| | | 1-palmitoyl-2-arachidonoyl-GPE (16:0/20:4)* | LR | LG |
| | | 1-palmitoyl-2-linoleoyl-GPE (16:0/18:2) | LR | LG |
| | | 1-palmitoyl-2-oleoyl-GPE (16:0/18:1)* | | LG |
| | | 1-oleoyl-2-linoleoyl-GPE (18:1/18:2)* | | G |
| Nucleotide | Purine Metabolism | inosine | G | R |
| | | adenine | | R |
| | Pyrimidine Metabolism | uracil | R | LR |
| Cofactors and Vitamins | Nicotinate and Nicotinamide Metabolism | trigonelline (N'-methylnicotinate) | | G |
| Xenobiotics | Benzoate Metabolism | catechol sulfate | | G |
| | | 4-vinylphenol sulfate | | G |
| | Food Component/Plant | equal sulfate | | G |
| | | stachydrine | G | G |

Fold change: G <0.5 | LG 0.5-1.0 | LR 1.0-2.0 | R >2.0

```
                         SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: mGapdh Forward Primer

<400> SEQUENCE: 1
aactttggca ttgtggaagg                                             20

<210> SEQ ID NO 2
<211> LENGTH: 20
<212> TYPE: DNA
<213> ORGANISM: Artificial Sequence
<220> FEATURE:
<223> OTHER INFORMATION: mGapdh Reverse Primer

<400> SEQUENCE: 2
ggatgcaggg atgatgttct                                             20

<210> SEQ ID NO 3
<211> LENGTH: 20
<212> TYPE: DNA
<213> ORGANISM: Artificial Sequence
<220> FEATURE:
<223> OTHER INFORMATION: mIFNy Forward Primer

<400> SEQUENCE: 3
gcgtcattga atcacacctg                                             20

<210> SEQ ID NO 4
<211> LENGTH: 20
<212> TYPE: DNA
<213> ORGANISM: Artificial Sequence
<220> FEATURE:
<223> OTHER INFORMATION: mIFNy Reverse Primer

<400> SEQUENCE: 4
gagctcattg aatgcttggc                                             20

<210> SEQ ID NO 5
<211> LENGTH: 20
<212> TYPE: DNA
<213> ORGANISM: Artificial Sequence
<220> FEATURE:
<223> OTHER INFORMATION: mIL-4 Forward Primer

<400> SEQUENCE: 5
tctcgaatgt accaggagcc                                             20

<210> SEQ ID NO 6
<211> LENGTH: 20
<212> TYPE: DNA
<213> ORGANISM: Artificial Sequence
<220> FEATURE:
<223> OTHER INFORMATION: m-IL-4 Reverse Primer

<400> SEQUENCE: 6
```

```
ggtgttcttc gttgctgtga                                              20

<210> SEQ ID NO 7
<211> LENGTH: 22
<212> TYPE: DNA
<213> ORGANISM: Artificial Sequence
<220> FEATURE:
<223> OTHER INFORMATION: mENT1 Forward Primer

<400> SEQUENCE: 7
cagcctcagg acaggtataa gg                                           22

<210> SEQ ID NO 8
<211> LENGTH: 23
<212> TYPE: DNA
<213> ORGANISM: Artificial Sequence
<220> FEATURE:
<223> OTHER INFORMATION: mENT1 Reverse Primer

<400> SEQUENCE: 8
gtttgtgaaa tacttggttg cgg                                          23

<210> SEQ ID NO 9
<211> LENGTH: 20
<212> TYPE: DNA
<213> ORGANISM: Artificial Sequence
<220> FEATURE:
<223> OTHER INFORMATION: mCNT2 Forward Primer

<400> SEQUENCE: 9
ttcacgaagg cgagaagttt                                              20

<210> SEQ ID NO 10
<211> LENGTH: 20
<212> TYPE: DNA
<213> ORGANISM: Artificial Sequence
<220> FEATURE:
<223> OTHER INFORMATION: mCNT2 Reverse Primer

<400> SEQUENCE: 10
ccaaagattc aggtgggtgt                                              20
```

USE OF INOSINE FOR THE TREATMENT OF T-REG DEFICIENCY

CROSS-REFERENCE TO RELATED APPLICATION

This application is a national phase entry pursuant to 35 U.S.C. § 371 of International Application No. PCT/EP2017/062800, filed May 26, 2017, which claims the benefit of U.S. Provisional Application No. 62/342,508, filed May 27, 2016, each of which is incorporated by reference herein in its entirety for any purpose.

SEQUENCE LISTING

The present application is filed with a Sequence Listing in electronic format. The Sequence Listing is provided as a file entitled "2018-11-26_01189-0005-00US_SeqList.txt" created on Nov. 26, 2018, which is 2,357 bytes in size. The information in the electronic format of the sequence listing is incorporated herein by reference in its entirety.

FIELD OF THE INVENTION

This invention relates to certain uses of inosine in the treatment of humans. This invention further relates to a method for the selection of specific bacterial strains, including lactic acid bacterial strains, capable of stimulating inosine production and the use of such strains to deliver beneficial effects for a host organism.

BACKGROUND OF THE INVENTION

Inosine is a nucleoside that is formed when hypoxanthine is attached to a ribose ring and is commonly found in tRNAs. Inosine is known to have potent immunomodulatory and neuroprotective effects and is available commercially as a dietary supplement. Inosine produces uric acid after ingestion and is suggested to be a natural antioxidant. Inosine has been studied in several clinical trials in, e.g. Parkinson's disease and multiple sclerosis.

Probiotics are defined as microorganisms that provide health benefits when consumed. For example, The Food and Agricultural Organization of the United Nations define probiotics as "live microorganisms which when administered in adequate amounts confer a health benefit on the host". Certain strains of lactic-acid producing bacteria such as *Lactobacillus* and Bifidobacteria are commonly used as probiotics in various types of foods, for example yoghurt. Growth and colonization of harmful microorganisms can be prevented by lactic acid producing bacteria through their own colonization on or inside the mammal, through formation of biofilms, through competition of available nutrients and also the production of specific substances such as hydrogen peroxides, bacteriocines, or organic acids (including lactic acid and acetic acid) that lower the pH. Some strains of for example lactic acid bacteria have also been shown to have effect in the treatment regimes of inflammatory disorders and also to have effects on the immune maturation and homeostasis of the host.

The regulatory T cells (Tregs), are a subpopulation of T cells which modulate the immune system, maintain tolerance to self-antigens, and abrogate autoimmune disease. Tregs generally suppress or down regulate induction and proliferation of effector T cells. Regulatory T cells come in many forms with the most well-understood being those that express CD4, CD25, and Foxp3 (CD4+CD25+ regulatory T cells). Genetic mutations in the gene encoding Foxp3 have been identified in both humans and mice based on the heritable disease caused by these mutations. Humans with mutations in Foxp3 suffer from a severe and rapidly fatal autoimmune disorder known as Immune dysregulation, Polyendocrinopathy, Enteropathy X-linked (IPEX) syndrome.

SUMMARY OF THE INVENTION

The present invention is based on the surprising finding that inosine alone can compensate for Treg deficiency or Treg dysfunction, when studying the scurfy mouse model, which is a model for immunodysregulation polyendocrinopathy enteropathy X-linked syndrome (IPEX syndrome) due to a mutation of Foxp3.

It is therefore an object of the invention to use a product comprising inosine to compensate for Treg dysfunction or Treg deficiency, for example in the treatment of IPEX. This is an advantageous finding for therapy of various diseases that have some kind of Treg-dysfunction or even in cases where there is a lack of or reduced numbers of Treg-cells.

The present invention is further based on the surprising finding that certain strains of lactic acid bacteria, in particular strains of *Lactobacillus reuteri*, are capable of stimulating in vivo inosine production. Indeed, to the inventors' knowledge, probiotics have not before been reported to produce inosine or to stimulate inosine production in vivo. The present invention thus also provides a new method of selecting specific bacterial strains, including strains of lactic acid bacteria, that are effective in stimulating or inducing inosine production in vivo.

Thus, in one aspect the present invention provides inosine for use in the treatment of a disease associated with Treg deficiency or Treg dysfunction.

In another aspect, the present invention provides a method of treating a disease associated with Treg deficiency or Treg dysfunction in a subject, said method comprising the step of administrating an effective amount of inosine to said subject.

In another aspect, the present invention provides the use of inosine in the manufacture of a medicament or composition for use in the treatment of a disease associated with Treg deficiency or Treg dysfunction.

In some embodiments, and as described in more detail elsewhere herein, the inosine can be provided by administration of a bacterial strain. Thus, in some embodiments, inosine is provided by the administration of a bacterial strain, e.g. a lactic acid bacterial strain, that is capable of stimulating or inducing the production of inosine.

Figure 3:
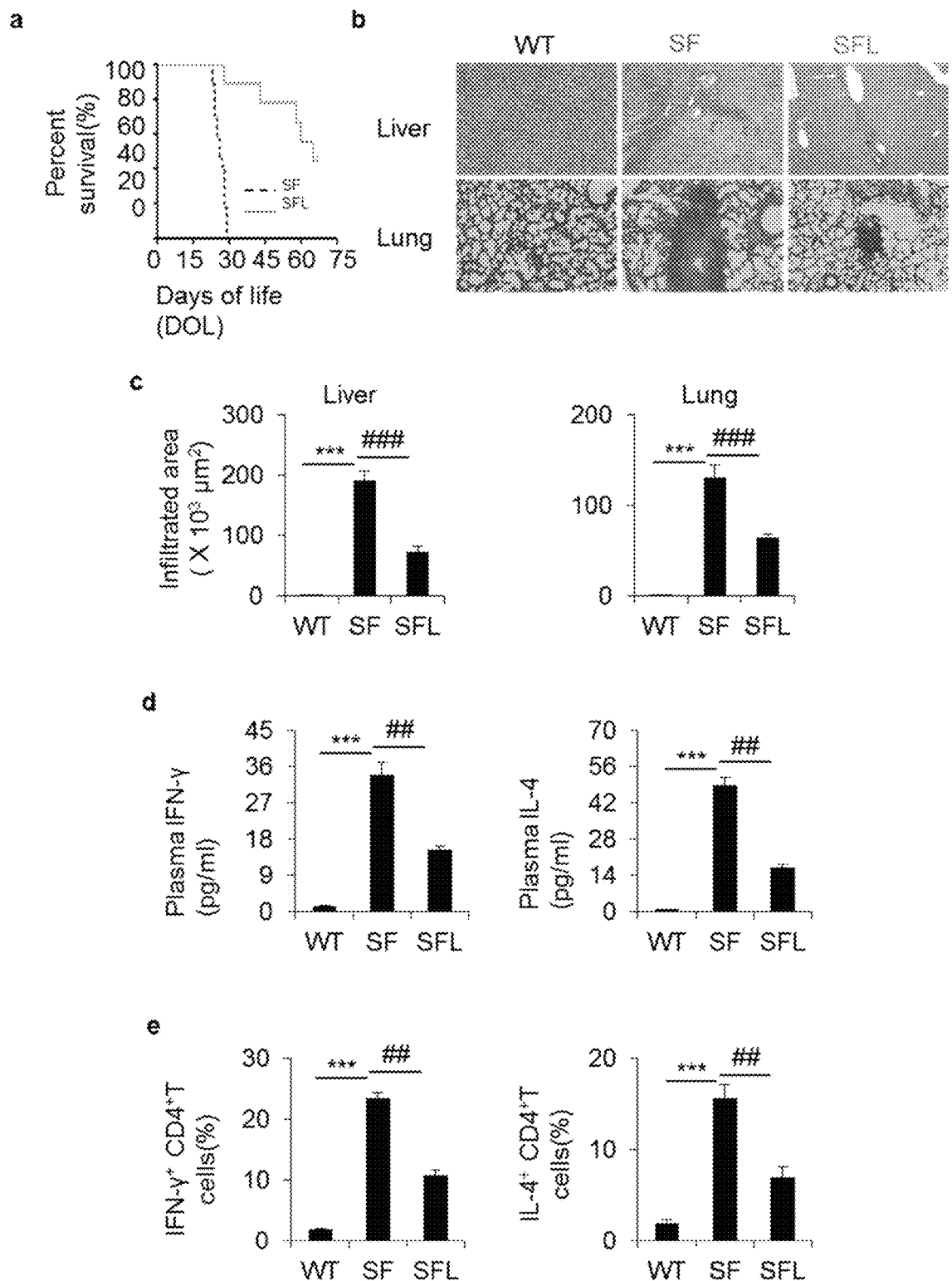

FIG. 3: *L. reuteri* treatment results: late treatment prolongs survival and inhibits inflammation in SF mice. a, Survival curves of SF (n=17) compared to SF with *L. reuteri* treatment (SFL, n=10) from d15 to d38. b, Representative H&E staining of liver and lung of WT, SF and SFL mice. c, Quantitation of inflammatory infiltrates in liver (left) and lung (right) of WT (n=12), SF (n=12) and SFL (n=10) mice. d, Levels of IFN-γ and IL-4 in plasma. e, The proportion of IFN-γ or IL-4-producing-CD4$^+$ T cells in spleen. Error bars, means±s.e.m. ***p<0.001. SF vs. WT. ##p<0.01, ###p<0.001. SFL vs. SF.

Figure 4:
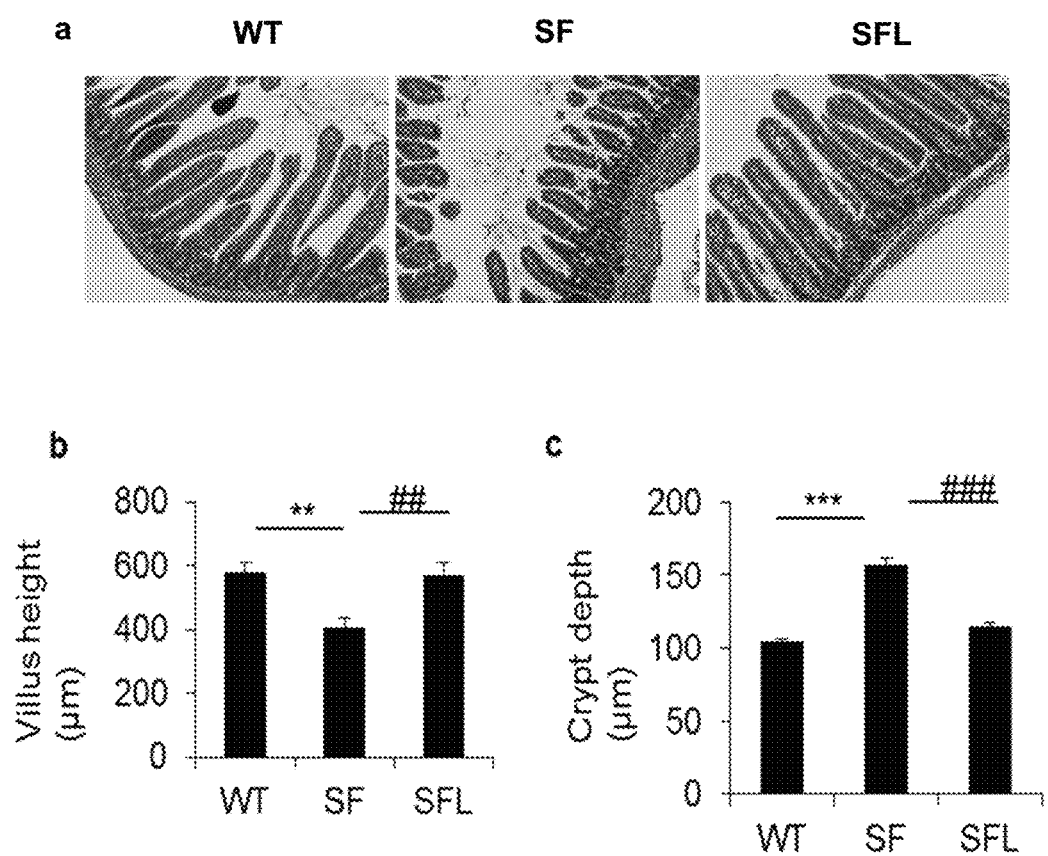

FIG. 4: *L. reuteri* treatment results: early treatment improves villus height and crypt depth in small intestine of SF mice. a, Representative H&E staining of small intestine of WT, SF and SFL mice. b, c, Mean villus height (b) and crypt depth (c) in WT (n=12), SF (n=12) and SFL (n=10). Error bars, means±s.e.m. p<0.01, *p<0.001. SF vs. WT. ##p<0.01, ###p<0.001. SFL vs. SF.

Figure 5:
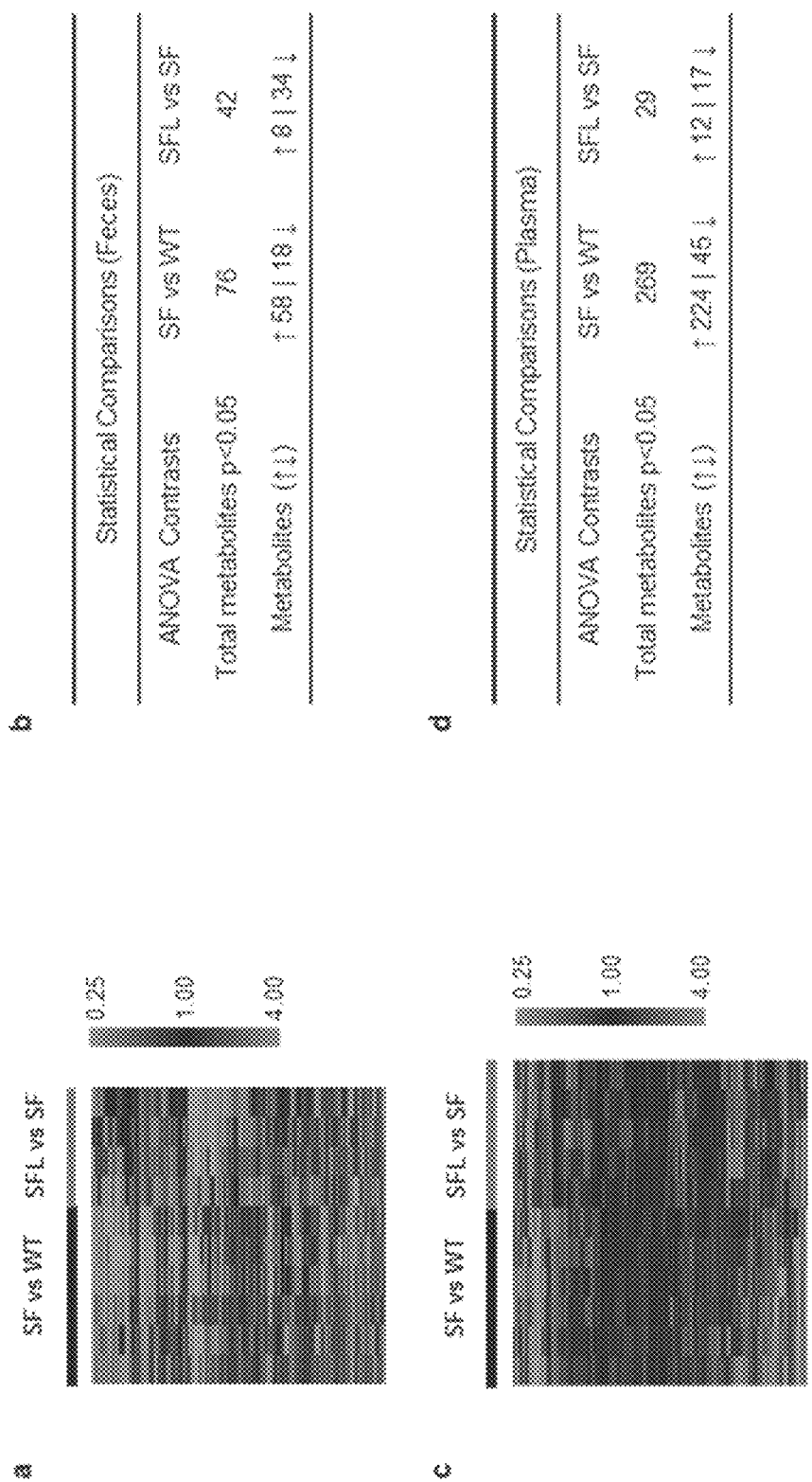

FIG. 5: *L. reuteri*: early treatment alters metabolomic profiles of feces and plasma disrupted by Treg-deficiency in SF mice. a, Heat map of 657 metabolites in feces of WT (n=6), SF (n=6) and SFL (n=4) mice. The scale bar indicates fold change of SF vs. WT or SFL vs. SF. b, Numbers of fecal metabolites affected, either up-regulated (↑) or down-regulated (↓) (p<0.05), by SF vs. WT or SFL vs. SF mice. c, Heat map of 525 metabolites in plasma of WT (n=6), SF (n=6) and SFL (n=5) mice. The scale bar indicates fold change of SF vs. WT or SFL vs. SF. d, Numbers of plasma metabolites affected, either up-regulated (↑) or down-regulated (↓) (p<0.05), by SF vs. WT or SFL vs. SF mice. e, Heat map showing the levels of 29 plasma metabolites that were significantly altered in SF mice with *L. reuteri* early treatment. Colors indicate fold change (SF vs. WT or SFL vs. SF). All changes indicated are p<0.05 by two-way ANOVA with contrasts. G=green, LG=light green, LR=light red, R=red.

Figure 6:
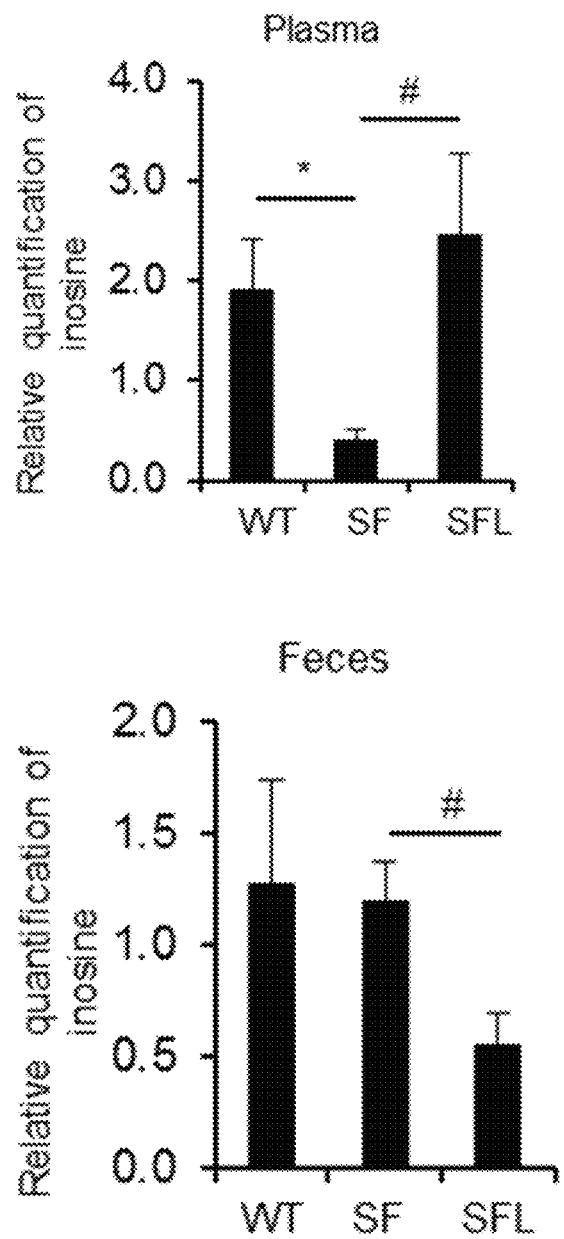

FIG. 6: Relative quantitation of inosine in plasma and feces. Graphs showing relative quantification of metabolites of inosine in plasma (a) and feces (b) of WT (n=6), SF (n=6) and SFL (n=5) mice. Error bars, means±s.e.m. *p<0.05, SF vs. WT. #p<0.05, SFL vs. SF.

Figure 7:
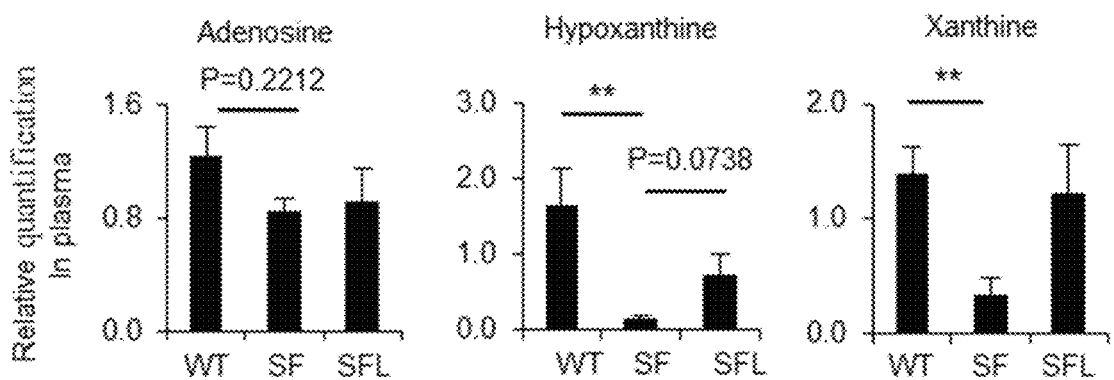
Figure 7:
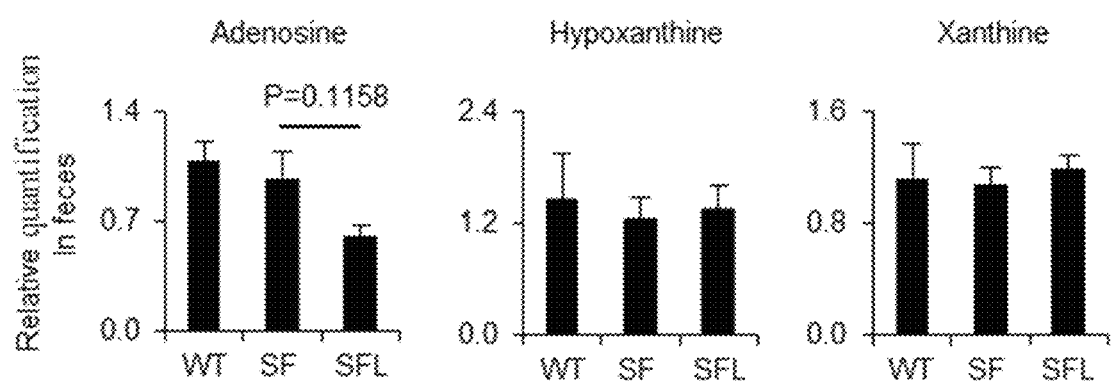

FIG. 7: The effect of *L. reuteri* early treatment on inosine metabolism pathway in SF mice. a, b, Graphs showing relative quantification of metabolites of inosine metabolism pathway in plasma (a) and feces (b) of WT (n=6), SF (n=6) and SFL (n=5) mice. Error bars, mean±s.e.m. **p<0.01. SF vs. WT.

Figure 8:
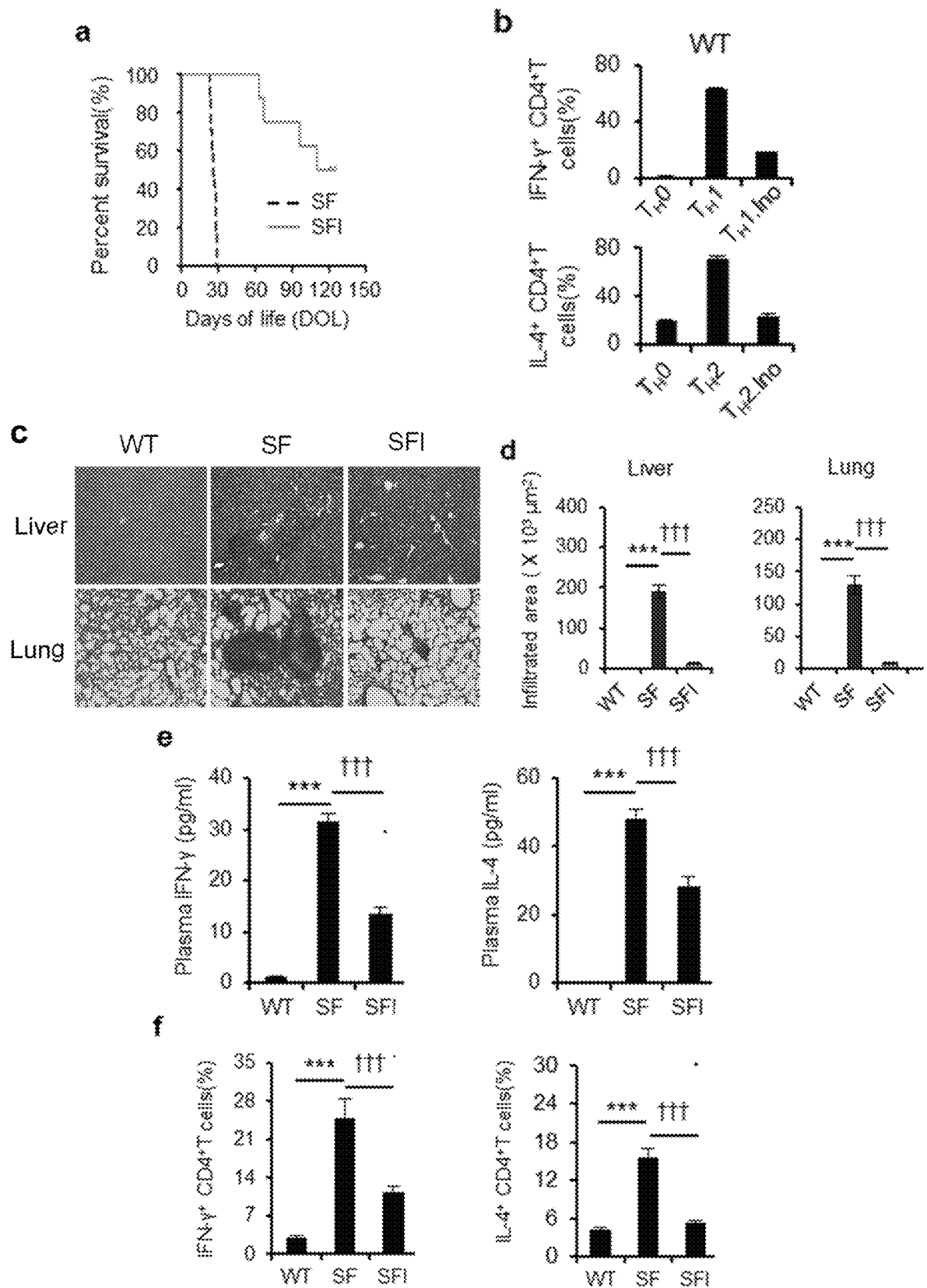

FIG. 8: Inosine suppresses $T_H1/T_H2$ differentiation and autoimmunity in SF mice. Survival curves of inosine-treated SF mice (SFI, n=8) vs. SF (n=17). b, Effect of inosine on differentiation of $T_H1$ and $T_H2$ cells from WT mice in vitro (n=3). c, Representative H&E staining of liver and lung of WT, SF and SFI. d, Quantification of inflammatory infiltrates in liver and lung of WT (n=12), SF (n=12) and SFI (n=8). e, Levels of IFN-γ and IL-4 in plasma. f, Proportion of splenic IFN-γ or IL-4-producing-CD4$^+$ T cells. Error bars, means±s.e.m. *p<0.05, ***p<0.001. SF vs. WT. †††p<0.001. SFI vs. SF.

Figure 9:
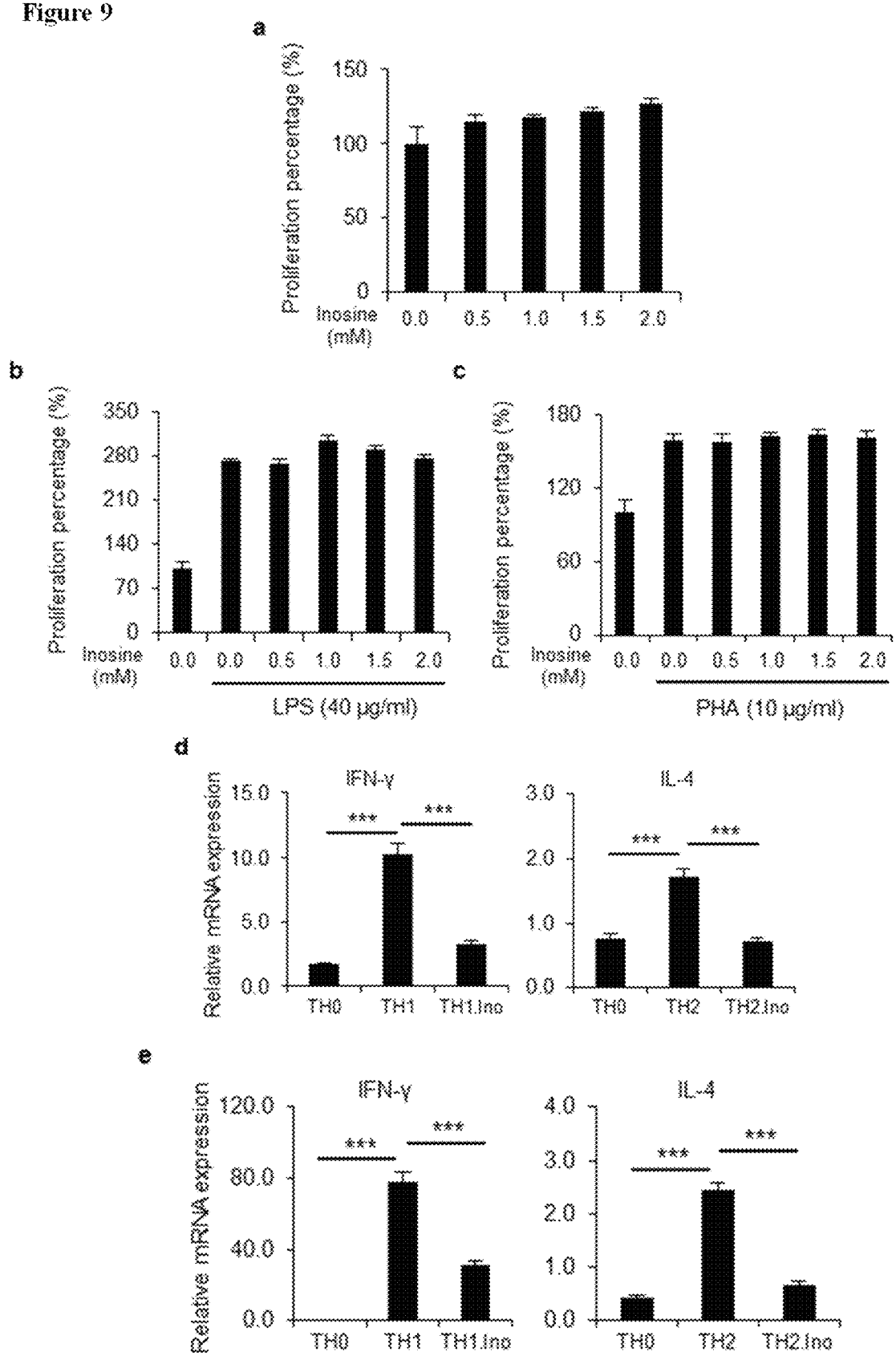

FIG. 9: Inosine does not inhibit the proliferation of B and T-lymphocytes but inhibits expression of IFNγ and IL-4 in $T_H1$ and $T_H2$, respectively. a, The cell viability of total lymphocytes with inosine treatment in the indicated concentration after 96 h (n=4). b, The effect of inosine on the proliferation of LPS-stimulated B-lymphocytes after 96 h treatment (n=4). c, The effect of inosine on the proliferation of PHA-stimulated T-lymphocytes after 96 h treatment (n=4). d, Relative mRNA expression of IFN-γ in $T_H1$ (left) or IL-4 in $T_H2$ (right) with 2 mM of inosine treatment after 24 h, respectively (n=4). e, Relative mRNA expression of IFN-γ in $T_H1$ (left) or IL-4 in $T_H2$ (right) with 2 mM of inosine treatment after 72 h, respectively (n=4). ***p<0.001.

DETAILED DESCRIPTION OF THE INVENTION AND PREFERRED EMBODIMENTS THEREOF

As described above, the present invention provides inosine for use in the treatment of a disease associated with Treg deficiency or Treg dysfunction.

Inosine can be administered in any appropriate way and in any appropriate form, including as a chemical entity per se, for example alone or as part of a product, e.g. a composition or pharmaceutical composition, which contains inosine as an active component. Some appropriate inosine containing compositions or products are commercially available, e.g. as oral formulations (e.g. capsules) or injectable formulations (e.g. ampoules).

For example, inosine can conveniently be provided as a dry powder, e.g. for oral administration. Such preparations of inosine might be encapsulated in capsules or be provided as tablets, e.g. 100 or 500 mg capsules or tablets. The daily dose (e.g. for a human subject) can be any appropriate effective dose, for example can be in a range from 100 mg to 2000 or 3000 mg. Inosine can also be administrated by intravenous or intramuscular injection (or other parenteral routes of administration), for example after reconstitution of a dry form of inosine. In such embodiments, inosine might be administered at a dose, e.g. a daily dose, of up to 500 mgs, e.g. up to 100 mgs, 200 mgs, 300 mgs, 400 mgs, or 500 mgs. Such doses can be administered in any appropriate volume, conveniently volumes of up to 10 mls, e.g. in volumes of up to 1 ml, 2 ml, 5 ml or 10 mls or doses of 20 to 100 mg/ml.

The inosine may be administered as the sole active component or administered with other active components.

In an alternative, any agent capable of stimulating inosine production (e.g. in vivo) can be used in the therapeutic methods of the invention. For example, in a preferred embodiment of the invention, a bacterial strain capable of stimulating inosine production in vivo, is used.

The present invention thus provides a new method of selecting bacterial strains, in particular strains of lactic acid bacteria, which are useful as probiotics and as pharmaceuticals in therapy. Such strains are selected for their ability to stimulate inosine production, in particular for their ability to stimulate inosine production in vivo upon administration to a subject. The strains for use in the methods of the present invention can stimulate or induce inosine production in any appropriate way. For example, the invention includes embodiments where the bacterial strains themselves are capable of producing inosine directly, e.g. secrete inosine, or embodiments where the bacterial strains stimulate or induce inosine production indirectly. The strains for use in the methods of the present invention can also modulate inosine utilization by e.g altering the uptake/excretion, e.g from the GI tract. Thus, appropriate strains for use in the present invention are those which can result in an increase in inosine levels in the subject in question.

One aspect of the present invention thus provides a method for the selection of a bacterial strain, preferably a lactic acid bacterial strain, capable of stimulating inosine production, wherein said method comprises:

a) Administering a bacterial strain to be tested, e.g. a lactic acid bacterial strain, to a suitable animal model, e.g. a mouse model, e.g. a scurfy mouse model;

b) Obtaining samples, e.g. plasma and/or stool samples from said animal model, e.g. mouse model;

c) Measure metabolites, e.g. plasma and/or stool metabolites, e.g. by metabolomic analysis, e.g. a non-targeted metabolomic analysis platform;

d) Selecting bacterial strains which are capable of stimulating inosine production.

One of the metabolites analysed or quantified in step c) will be inosine so that bacterial strains which are capable of stimulating inosine production can be selected in step d). In other embodiments, step c) can comprise the measurement or analysis of inosine alone or with other metabolites by any appropriate method. Preferred methodology for carrying out one or more of such steps are outlined in the Examples. In preferred embodiments plasma (or other systemic samples, e.g. peripheral blood or serum) is analysed.

Viewed alternatively, the present invention provides a method for the selection of a bacterial strain, preferably a lactic acid bacterial strain, by screening a bacterial strain, e.g. a lactic acid bacterial strain, for its ability to stimulate inosine production, and selecting a strain which has that ability. Preferred method steps are outlined above.

Bacterial strains with the ability to stimulate high or significant or increased levels of inosine, e.g. levels in the plasma or the GI tract, e.g. in comparison to the levels observed in the absence of said bacterial strain, are preferred, for example bacterial strains that stimulate inosine production at a level which is therapeutically effective in a subject. Thus, in preferred embodiments a bacterial strain is selected for its ability to stimulate inosine production in vivo and in preferred embodiments the selection methods are in vivo methods.

As preferred bacterial strains for use in the invention have the ability to stimulate inosine production in vivo, a preferred option is to assess the strains in an appropriate experimental in vivo assay, e.g. using an appropriate mouse or other experimental animal model, e.g. a scurfy mouse model. Appropriate methods of measuring stimulation of inosine production by strains of bacteria and levels of inosine production, e.g. in the plasma, stool or GI tract, would be well known to a person skilled in the art. For example, methods of relative quantification of inosine production in appropriate mouse models and comparing levels produced in wild type mice, disease model mice, and mice to which bacterial strains have been administered, are described in the Examples.

Thus, in some embodiments of the invention, the selection method will involve the step of detecting or determining the amount or level (e.g. the concentration, level, or relative level) of inosine stimulation by a candidate bacterial strain, e.g. in comparison to inosine stimulation where no bacterial strain is present. Because of the downstream uses of the bacterial strains which are selected by the methods of the invention, after bacterial strains capable of stimulating inosine production are selected or isolated, other embodiments will involve the further steps of culturing or propagating or producing such bacterial strains and optionally formulating said cultured or propagated or produced strains into a composition comprising said strain, e.g. a pharmaceutical or nutritional composition, e.g. as described elsewhere herein, or possibly storing such bacterial strains for future uses, for example through lyophilisation or freeze drying, after which they may be cultured, etc., and optionally formulated, etc., as described above.

In embodiments where more than one bacterial strain is screened using the methods of the invention, the amount of inosine generated can be quantified (e.g. in an absolute or relative manner) and the bacterial strain, e.g. the lactic acid bacterial strain, which stimulates the production of the highest amount or level or concentration of inosine can be selected. Alternatively, any bacterial strains which are capable of stimulating increased (preferably significantly increased) levels of inosine, e.g. in comparison to the levels observed in the absence of said bacterial strain, can be selected.

Once an appropriate bacterial strain has been selected using the method of the present invention it can then be used for stimulating the production, e.g. the local or systemic production (or increase), of inosine in a subject. Said bacterial strains thus also have to be capable of stimulating the production, e.g. the local or systemic production, of inosine in a subject, i.e. in vivo.

In any of the selection methods of the invention which are carried out in vivo, e.g. using an in vivo non-human animal model, such methods are experimental methods and are not performed for the purposes of therapy or surgery, e.g. are not practiced as methods of treatment of the human or animal body by surgery or therapy or are non-therapeutic or non-surgical methods.

A further aspect of the invention thus provides the use of a bacterial strain of the invention or a bacterial strain selected, obtained or obtainable by the selection method of the invention, in a method for stimulating the production of inosine, e.g. in vivo. The invention thus provides a method of stimulating the production of inosine in vivo, said method comprising the administration to a subject of a bacterial strain that is capable of stimulating the production of inosine in vivo. The selection methods of the invention can also be used to select new bacterial strains which are suitable for use in therapy as described herein, wherein said strains are capable of stimulating the production of inosine in vivo.

Thus, the inosine can be provided by use of a bacterial strain. For example, said strain can stimulate the production of inosine (e.g. by an indirect mechanism where the bacterial strain increases inosine levels by some means involving a further component or entity or process other than the strain itself, e.g. by inducing other cells to release inosine or by promoting absorption of inosine such that circulatory levels, e.g. blood/plasma levels, of inosine are increased). This will thus lead to a systemic increase of inosine. In another example, said strain can modulate inosine utilization by e.g altering the uptake/excretion, e.g from the GI tract.

Thus, a further aspect of the present invention provides a bacterial strain, e.g. a lactic acid bacterial strain, selected, obtained or obtainable by the selection method of the invention, wherein said strain is capable of stimulating or inducing the production of inosine, for use in the production, e.g. local or systemic production (or increase), of inosine in a subject. Thus, said strains can stimulate or induce production of inosine (or increased levels of inosine) in vivo.

Alternative embodiments of the invention provide a bacterial strain, e.g. a lactic acid bacterial strain, wherein said strain is capable of stimulating or inducing the production of inosine, for use in the production, e.g. local or systemic production (or increase), of inosine in a subject. Thus, said strains can stimulate or induce production of inosine (or increased levels of inosine) in vivo.

Preferred features of this bacterial strain and its uses, e.g. therapeutic uses, are described elsewhere herein. For example, preferred diseases to be treated in accordance with such embodiments are described elsewhere herein.

Thus, as will be outlined elsewhere herein, preferred uses are in the treatment of diseases which will benefit from inosine production (or increased levels of inosine), for example diseases associated with a deficiency or reduction in inosine or diseases associated with Treg deficiency or Treg dysfunction.

Methods of treatment or methods for stimulating the production, e.g. local or systemic production (or increase), of inosine in a subject, are also provided, said methods comprising the administration of a bacterial strain, e.g. a lactic acid bacterial strain, selected, obtained or obtainable by the selection method of the invention, or the administration of a bacterial strain, e.g. a lactic acid bacterial strain, wherein said strain is capable of stimulating or inducing the production of inosine, to said subject in an amount effective to stimulate production, e.g. local or systemic production, or increased level, of inosine in said subject. Preferred features of the strain and its therapeutic uses are described elsewhere herein. For example, preferred diseases to be treated in accordance with such embodiments are described elsewhere herein.

Also provided by the present invention is the use of a bacterial strain, e.g. a lactic acid bacterial strain, selected, obtained or obtainable by the selection method of the invention, wherein said strain is capable of stimulating or inducing the production of inosine, in the manufacture of a composition or medicament for use in the production, e.g. local or systemic production, or increased level, of inosine in a subject. Alternative embodiments provide the use of a bacterial strain, e.g. a lactic acid bacterial strain, wherein said strain is capable of stimulating or inducing the production of inosine, in the manufacture of a composition or medicament for use in the production, e.g. local or systemic production, or increased level, of inosine in a subject. Such uses are therapeutic uses and preferred features of the strain and its therapeutic uses are described elsewhere herein. For example, preferred diseases to be treated in accordance with such embodiments are described elsewhere herein.

Products or compositions comprising said bacterial strains and uses of said products or compositions in methods and uses as described herein form yet further aspects of the invention.

Alternative and preferred embodiments and features of the invention as described elsewhere herein apply equally to the methods of treatment, uses and products of the invention.

A bacterial strain, e.g. a lactic acid bacterial strain, selected, obtained or obtainable by the selection methods of the invention, wherein said strain is capable of stimulating the production of inosine (e.g. in vivo), is a yet further aspect of the invention. Therapeutic uses of the strains selected by the present invention are also provided. In preferred such embodiments of the invention the strain selected, obtained, obtainable or used is not *Lactobacillus reuteri* DSM 17938.

Any appropriate bacterial strain, e.g. probiotic bacterial strain, for example any probiotic bacteria, can be subjected to the selection methods of the invention and any appropriate bacterial strain, e.g. probiotic bacterial strain, which is capable of stimulating the production of inosine (or increasing the levels of inosine) can be used in the methods or uses of the present invention, e.g. in the therapeutic methods or uses described herein. Such strains can thus be used for the in vivo production or local or systemic production (or increasing levels) of inosine in a subject.

Preferred bacterial strains are lactic acid bacteria, e.g. *Lactobacillus*. Particularly preferred bacterial strains are *Lactobacillus reuteri*. Thus, a yet further aspect of the invention provides the use of such strains to treat one or more of the diseases as described herein. In some embodiments of the invention the strain used is not *Lactobacillus reuteri* DSM 17938. The *Lactobacillus reuteri* DSM 17938 strain was deposited under the Budapest Treaty at the DSMZ-Deutsche Sammlung von Mikroorganismen and Zellkulturen GmbH (Mascheroder Weg 1b, D-38124 Braunschweig) on 30 Jan. 2006. Such bacterial strains can be isolated strains or pure cultures. In some embodiments such strains will not correspond to naturally occurring bacterial strains.

As set out above, the inosine or the bacterial strains as described herein, or the strains selected by or obtainable by the selection methods of the invention, have uses in therapy. Thus, a further aspect of the invention provides inosine or the inosine stimulating strains as described herein, or strains which are selected, obtained or obtainable using the selection methods of the invention, for use in the production, e.g. local or systemic production, of inosine in a subject. In preferred embodiments of the invention, said inosine or inosine stimulating strains is used for the treatment of a disease (or condition) which will benefit from production or increased production, e.g. local or systemic production, of inosine. In other embodiments, said inosine or inosine stimulating strains is used for the treatment of a disease (or condition) which can be treated with the administration, e.g. local or systemic administration, of inosine. Exemplary diseases are those associated with a deficiency or reduction in inosine levels.

Production of inosine (or stimulation or induction of inosine production) as described herein refers in general to an increase in level (e.g. concentration) or amount of inosine in a subject. Such production can for example be local production and/or systemic production. Local production (or local levels of inosine) refers to amounts (or levels, e.g. concentration) of inosine at a site where inosine or a bacterial strain as described herein is administered, e.g. the GI tract, GU tract, oral cavity, etc. Systemic production (or systemic levels of inosine) refers to amounts (or levels, e.g. concentration) of inosine as found in the circulation, in particular in peripheral blood, plasma or serum.

Thus, when an increase in inosine is referred to herein, e.g. as caused by the stimulation of inosine production by a bacterial strain or by the direct administration of inosine or an inosine containing compound or product or composition, such an increase can refer to an increase in amount or level (e.g. concentration) of inosine. Preferably such increases are measurable increases, more preferably they are significant increases, preferably clinically significant or statistically significant increases, for example with a probability value of <0.05, when compared to an appropriate control level or value (e.g. compared to an untreated or placebo treated sample or subject, e.g. where no inosine is administered, or compared to a sample or subject where the bacterial strain is not present). For example, levels of inosine might be increased by at least 0.5 fold, 1 fold, 2 fold, 3 fold, 4 fold, 5 fold, 10 fold, or more as compared to an appropriate control level or value. Alternatively or additionally, the increases are such as to give rise to a therapeutic benefit or effect as described elsewhere herein, e.g. such as to inhibit or reduce the differentiation of TH1 and/or TH2 cells.

Such increases in inosine are generally observed in vivo and can for example be local increases and/or systemic increases. Local increase of inosine refers to increased amounts (or levels, e.g. concentration) of inosine at a site where inosine or a bacterial strain as described herein is administered, e.g. the GI tract, GU tract, oral cavity, etc. Systemic increase of inosine refers to increased amounts (or levels, e.g. concentration) of inosine as found in the circulation, in particular in blood, plasma or serum. Increased systemic levels are preferred and the invention provides therapeutic methods based on the systemic administration of inosine or an increase in systemic inosine, e.g. inosine in the blood, plasma or serum. Preferred diseases or conditions to be treated are described elsewhere herein.

In other embodiments, inosine or inosine stimulating bacterial strains as described herein, or bacterial strains which are selected, obtained or obtainable using the selection methods of the invention, can be used for the treatment of a disease associated with or characterised by Treg deficiency or a disease associated with or characterised by Treg dysfunction, e.g. Treg deficiency or Treg dysfunction induced (or mediated or associated) inflammatory disease or autoimmune disease. Exemplary diseases are those associated with or characterised by deficiency or dysfunction in Foxp3$^+$ Tregs. The inventors have shown that inosine can mimic the effect of Tregs on inhibiting or reducing the differentiation of CD4$^+$ cells e.g. TH1/TH2 cells. This effect on pro-inflammatory TH1/TH2 cells can result in inhibiting or reducing TH1/TH2 cell induced or mediated inflammation). Thus, whilst not wishing to be bound by theory, the present invention can be used to treat any diseases associated with Treg deficiency or Treg dysfunction, as the inosine which is administered or which is stimulated by the bacterial strains can substitute for (or compensate for) the lack of (or the dysfunctional) Tregs or mimic the Tregs which are absent or dysfunctional.

The therapeutic methods and uses of the present invention (or the methods and uses of inosine, including bacterial strains which stimulate inosine production as described herein) can be used to inhibit or reduce the differentiation of CD4+ T-cells, in particular TH1 and/or TH2 cells (and for example inhibit or reduce TH1/TH2 cell induced or mediated inflammation or immune response). Thus, other examples of diseases to be treated are those in which it is desirable to inhibit or reduce the differentiation of CD4+ T-cells, in particular TH1 and/or TH2 cells, or to inhibit or reduce TH1 and/or TH2 cell induced or mediated inflammation or immune response. The therapeutic methods and uses of the present invention (or the methods and uses of inosine, including bacterial strains which stimulate inosine production as described herein) can be used to treat autoimmune diseases.

Other examples of diseases to be treated are CD4+ T-cell driven diseases, in particular TH1 and/or TH2 cell driven diseases, e.g. diseases caused by or associated with abnormal (or aberrant or undesired) function or behaviour of, e.g. unregulated behaviour of, CD4+ T-cells, in particular TH1 and/or TH2 cells, for example autoimmune diseases or other inflammatory diseases (e.g. diseases associated with abnormal (or aberrant or undesired) or increased inflammation). Other diseases to be treated are those in which CD4+ T-cells, in particular TH1 and/or TH2 cells, are increased. Such an increase in CD4+ T-cells, e.g. TH1 and/or TH2 cells, observed in such diseases can be for example an increase in absolute numbers or proportions of CD4+ T-cells, e.g. TH1 and/or TH2 cells, or for example an increase in the levels of the cytokines produced by CD4+ T-cells, e.g. TH1 and/or TH2 cells. Such increases in CD4+ cells, in particular TH1 and/or TH2 cells, or increases in cytokines can be observed in the plasma or in other parts of the subject, e.g. the spleen or lymph nodes. An exemplary cytokine which is characteristic of TH1 cells and can be measured is IFN-γ and an exemplary cytokine which is characteristic of TH2 cells and can be measured is IL-4.

Tregs are a subpopulation of T cells which modulate the immune system, maintain tolerance to self-antigens, and abrogate autoimmune disease. Tregs generally suppress or down regulate induction and proliferation of effector T cells. Regulatory T cells come in many forms with the most well-understood being those that express CD4, CD25, and Foxp3 (CD4+CD25+ regulatory T cells). Genetic mutations in the gene encoding Foxp3 have been identified in both humans and mice based on the heritable disease caused by these mutations. Humans with mutations in Foxp3 suffer from a severe and rapidly fatal autoimmune disorder known as Immune dysregulation, Polyendocrinopathy, Enteropathy X-linked (IPEX) syndrome.

Thus, further examples of diseases (or conditions) associated with Treg dysfunction or Treg deficiency which can be treated in accordance with the present invention are:
  IPEX
  A disease associated with a mutation or alteration in Foxp3
  IPEX-like syndromes, for example due to or associated with mutations in one or more of: CTLA4, CD25, STAT1, STAT5b, ITCH and IL-2Rb.

Viewed another way, the present invention further provides inosine or inosine stimulating bacterial strains as described herein, or bacterial strains which are selected, obtained or obtainable using the selection methods of the invention, for use in the treatment of a disease or condition as described herein, in particular the treatment of IPEX, a disease associated with a mutation or alteration in Foxp3, or IPEX-like syndromes, for example due to or associated with mutations in one or more of: CTLA4, CD25, STAT1, STAT5b, ITCH and IL-2Rb.

In all embodiments described herein the term "disease(s) associated with" or "condition(s) associated with" can also refer to "disease(s) (or condition(s)) characterised by" or "disease(s) (or condition(s)) caused by".

The therapeutic uses of inosine (including bacterial strains which stimulate inosine production) as described herein generally result in the reduction or alleviation of the relevant disease or symptoms of disease, for example can result in an increased or prolonged survival time. Said uses can result in a significant increase in levels of inosine in the subject or a reduced immune response (e.g. reduced inflammation or a reduced immune response mediated by effector T cells such as TH1 and/or TH2 cells) or reduced autoimmunity. As described elsewhere herein, the increase in levels of inosine (or the methods and uses of inosine, including bacterial strains which stimulate inosine production as described herein) can also compensate for a lack of Treg cells or can mimic Treg cells and can result in a suppressed or reduced immune response, e.g. an inhibition or reduction in differentiation of CD4$^+$ effector cells, in particular TH1 and/or TH2 cells. This can for example be observed or assessed by any appropriate method which would be well known to a person skilled in the art, for example, by looking for a decrease or reduction in IL-4 (TH2) and/or IFN-γ (TH1) levels, e.g. in the plasma of a subject after therapy, or a decreased proportion (percent) or frequency or number of such TH1 and/or TH2 cells in the subject after therapy, e.g. in the plasma or spleen or lymph nodes of a subject.

In addition, embodiments of the invention involve the provision of increased circulatory inosine levels, e.g. in the blood/plasma of a subject. Such increased levels can be achieved by administering inosine intravenously or intramuscularly, or, alternatively, by for example inosine being absorbed more efficiently from the GI tract or released from other cells in the blood/plasma as an indirect consequence of the bacteria. Preferred embodiments of the invention involve bacterial strains which can increase or stimulate the absorption of inosine from a site of local administration of bacteria (e.g. GI tract) to blood/plasma. In this way increased inosine levels in blood/plasma (or increased systemic levels of inosine) are achieved.

Such reduction or alleviation of disease or symptoms thereof (e.g. clinical symptoms or severity, e.g. effects on survival) can thus be measured by any appropriate assay for the disease or symptom or parameter (e.g. levels of cytokines or types of T-cells or survival) in question, examples of which would be well known to a person skilled in the art, some examples of which are also shown in the Examples herein. Preferably the reduction or alleviation of disease or symptoms (or the change in one or more parameters, e.g. those described above) is measurable, and preferably significant, e.g. clinically significant or statistically significant, preferably with a probability value of <0.05. Such reduction or alleviation of disease or symptoms (or the change in one or more parameters, e.g. those described above) are generally determined compared to an appropriate control individual or population, for example a healthy animal or subject (or a population thereof) or an untreated or placebo treated animal or subject (or a population thereof), or, conveniently, the same individual subject before treatment.

The administration of the inosine (including bacterial strains which stimulate inosine production) as described herein in the methods of treatment and uses of the invention is carried out in pharmaceutically or physiologically effective amounts, to subjects (animals or mammals) in need of treatment. Thus, said methods and uses may involve the additional step of identifying a subject in need of treatment.

Treatment of disease or conditions in accordance with the present invention (for example treatment of pre-existing disease) includes cure of said disease or conditions, or any reduction or alleviation of disease (e.g. reduction in disease severity) or symptoms of disease.

The methods and uses of the prevent invention are suitable for prevention of diseases or conditions as well as active treatment of diseases or conditions (for example treatment of pre-existing disease). Thus, prophylactic treatment is also encompassed by the invention. For this reason in the methods and uses of the present invention, treatment or therapy also includes prophylaxis or prevention where appropriate.

Such preventative (or protective) aspects can conveniently be carried out on healthy or normal or at risk subjects and can include both complete prevention and significant prevention. Similarly, significant prevention can include the scenario where severity of disease or symptoms of disease is reduced (e.g. measurably or significantly reduced) compared to the severity or symptoms which would be expected if no treatment is given.

A yet further aspect of the invention provides inosine (including bacterial strains which stimulate inosine production) for the therapeutic uses as defined elsewhere herein, wherein said use further comprises the administration of at least one further agent, e.g. a therapeutic or nutritional agent. In embodiments where bacterial strains are used, exemplary agents might be substrate components or other components which will increase or enhance the stimulation of the production of inosine by said bacterial strain, or a source of such components. A carbon source to support the metabolic activity of the bacteria can also be added to the final formulation.

Said further agents can be administered together with the bacterial strains (e.g. as a combined preparation or a single composition) or can be administered separately. If administered separately, said further agents can be administered at the same time (or substantially the same time) as the bacterial strains, or at different time points. Suitable administration regimes and timings can readily be determined by the skilled person depending on the further agent in question.

The present invention also provides a composition comprising:
(i) a bacterial strain, e.g. a lactic acid bacterial strain, capable of stimulating the production of inosine, e.g. a lactic acid bacterial strain, selected, obtained or obtainable by the selection method of the invention; and
(ii) one or more substrate components or agents which will increase or enhance the stimulation of production of inosine, or a source of such components or agents.

The term "subject" as used herein includes any mammal, for example humans and any livestock, domestic or laboratory animal. Specific examples include mice, rats, pigs, cats, dogs, sheep, rabbits, cows, horses and monkeys. Preferably, however, the subject is a human subject. In embodiments relating to therapeutic methods and uses described herein, appropriate subjects are those having, suspected of having, or at risk of having the disease to be treated.

The methods and uses of the invention generally involve the administration of the inosine or the selected bacterial strain as defined herein, e.g. a lactic acid bacterial strain, to a subject, preferably a human.

Conveniently said administration is a form of local administration, e.g. oral, rectal, vaginal, topical or by tube-feeding. Thus, the inosine or bacterial strains as described herein can be administered to the GI tract, GU tract or oral cavity, as desired or appropriate. However, equally for some embodiments intravenous or intramuscular injection will be appropriate.

An appropriate mode of administration and formulation of the inosine or bacterial strains, etc., is chosen depending on the site where inosine or stimulation of inosine production, e.g. local production or systemic production, or increased production or increased levels of inosine, is desired. A preferred mode of administration is oral in order to e.g. facilitate or result in increased inosine levels in the gastrointestinal tract. As described elsewhere herein, such a mode of administration can also result in an increase in inosine levels in the blood/plasma and this is preferred in some embodiments. Where inosine (e.g. an inosine containing product or composition) is administered and an increase in inosine levels in the blood/plasma is desired, then intravenous or intramuscular injection can be appropriate.

Appropriate doses of the inosine (including bacterial strains which stimulate inosine production) as described herein, can readily be chosen depending on the disease (or condition) to be treated, the mode of administration and the formulation concerned. Thus, a dosage and administration regime is generally chosen such that the inosine or bacterial strains administered to the subject in accordance with the present invention can result in inosine levels or the stimulation of inosine production, e.g. local production or systemic production, or an increased production or increased levels of inosine, e.g. increased local production or systemic production, and to give rise to the desired therapeutic effects or health benefits (for example an increase in Tregs (or an increase in functional Tregs) or a compensation for lack of Tregs or Treg deficiency as described elsewhere herein, e.g. an inhibition or reduction in the differentiation of TH1 and/or TH2 cells, or an inhibition or reduction in autoimmunity, e.g. autoimmunity associated with Treg deficiency or dysfunction, or other reduced TH1 and/or TH2 cell mediated inflammation, or any other reduction or alleviation of the relevant disease or symptoms of disease for example as described elsewhere herein).

For example, in one embodiment of the invention, inosine is prepared as a dry powder, e.g. for oral administration. In such embodiments, inosine might be encapsulated in capsules, e.g. 100 or 500 ma capsules and the daily dose (e.g. for a human subject) can be in a range from 100 mg to 2000 or 3000 mg. Inosine can also be administered by intravenous or intramuscular injection, e.g. after reconstitution of a dry powder form of inosine. In such embodiments, inosine might be administered at a dose, e.g. a daily dose, of up to 500 mgs, e.g. up to 100 mgs, 200 mgs, 300 mgs, 400 mgs, or 500 mgs. Such doses can be administered in any appropriate volume, conveniently volumes of up to 10 mls, e.g. in volumes of up to 1 ml, 2 ml, 5 ml or 10 mls or doses of 20 to 100 mg/ml.

In embodiments where the inosine is provided to the subject by way of the administration of a bacterial strain, preferably said dosage is a therapeutically effective dosage which is appropriate for the type of animal and condition being treated. For example, daily doses of $10^4$ to $10^{13}$, for example $10^5$ to $10^9$, or $10^6$ to $10^8$, or $10^8$ to $10^{10}$, or $10^9$ to $10^{12}$ total CFUs of bacteria may be used. A preferred daily dose is around $10^8$ total CFUs, e.g. $10^7$ to $10^9$ or $10^8$ to $10^9$. Another preferred daily dose is around $10^{12}$ total CFUs, e.g. $10^{10}$ or $10^{11}$ to $10^{13}$, or $10^{11}$ to $10^{12}$ or $10^{12}$ to $10^{13}$.

"Inosine" as used herein is given its art understood meaning. It is a nucleoside that is formed when hypoxanthine is attached to a ribose ring and can be manufactured by methods which are well known and described in the art, e.g. by fermentation. The systematic (IUPAC) name for inosine is 9-[2R,3R,4S,5R)-3,4-dihydroxy-5-(hydroxymethyl)oxolan-2-yl]-6,9-dihydro-3H-purin-6-one. Inosine preparations for use in the present invention can be readily obtained, for example, inosine has been used in other pharmaceutical applications and inosine is commercially available as a dietary or nutritional supplement.

The inosine for use as described herein can be in the form of a product or composition containing inosine or a salt thereof, e.g. a pharmaceutically acceptable salt thereof, examples of which would be well known to those skilled in the art. For example, the inosine can be in the form of a composition (e.g. a pharmaceutical composition) comprising said inosine compound, together with one or more acceptable (e.g. pharmaceutically acceptable) carriers, excipients or diluents. Acceptable carriers, excipients and diluents, e.g. for therapeutic use, are well known in the art and can be selected with regard to the intended route of administration and standard practice. Examples include binders, lubricants, suspending agents, solvents, coating agents, solubilising agents, preserving agents, wetting agents, emulsifiers, surfactants, sweeteners, colourants, flavouring agents, odorants, buffers, antioxidants, stabilising agents and/or salts. Inosine containing compositions are well known and described in the art and any of these may be used.

The inosine compounds described herein may be formulated with one or more conventional carriers and/or excipients according to techniques well known in the art. For example, these may be formulated in conventional oral administration forms, e.g. tablets, coated tablets, capsules, powders, granulates, solutions, dispersions, suspensions, syrups, emulsions, etc. using conventional excipients, e.g. solvents, diluents, binders, sweeteners, aromas, pH modifiers, viscosity modifiers, antioxidants, etc. Suitable excipients may include, for example, corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose or fatty substances such as hard fats or suitable mixtures thereof, etc.

It is envisaged that the inosine compounds or compositions described herein can also be administered by other conventional administration routes, e.g. parenterally. Where parenteral administration is employed this may, for example, be by means of intravenous, subcutaneous or intramuscular injection.

The term "Treg" as used herein refers to regulatory T cells. Regulatory T cells (Tregs) play a critical role in maintaining the balance between immune activation and tolerance and thus in controlling the immune response and inflammation. Tregs are a suppressive subset of CD4$^+$ T helper cells and are important for the immune response regulation. Tregs are thus immunosuppressive and generally suppress or down regulate induction (e.g. differentiation) and proliferation of effector T cells such as TH1 and TH2 cells. Further, a key transcription factor, forkhead box P3 (FOXP3) is required for their development and proper function. T-regs are a different subset of CD4+ T cells to TH1 and TH2 cells. A person skilled in the art would readily be able to distinguish between these sub-types, e.g. through the use of characteristic cell surface markers. For example, Tregs can be distinguished from other sub-types of T-cells as they are positive for FOXP3 in addition to CD4.

"Treg-dysfunction" means that the regulatory T cells (Tregs) do not function properly (or function abnormally or aberrantly or in an undesired or pathological way) for example by loosing their control of the immune response, e.g. resulting in an uncontrolled immune response or immune activity. It includes an imbalance between Tregs and T effector cells, e.g. in which the T effector cells (e.g. TH1 and/or TH2 cells) are over reactive or over produced, e.g. resulting in an uncontrolled or increased immune response or inflammation (e.g. TH1 and/or TH2 cell mediated or induced inflammation). Treg-dysfunction can be a result of abnormal or aberrant or pathological FOXP3 function, for example caused by a mutation, alteration or other defect in FOXP3, e.g. the FOXP3 gene or protein).

"Treg-deficiency" means a lack of regulatory T cells (Tregs) and includes a reduction in numbers of Tregs from normal levels or a situation where not enough Tregs are produced. Treg deficiency, for example by the lack of FOXP3, results in the development of a disease called immune dysregulation, polyendocrinopathy, enteropathy, X-linked syndrome (IPEX) which is a severe autoimmune disease that starts early in infants.

Treg deficiency or dysfunction can be analyzed in animal models such as SF (scurfy) mice which have a deletion in the forkhead domain of Foxp3 and fail to develop thymic-derived Foxp3+ regulatory T cells (nTreg). This results in the development of a fatal lymphoproliferative syndrome with multi-organ inflammation.

An uncontrolled immune activity is problematic and can be detrimental and lead to many different types of severe conditions. Little is still known about regulation of Tregs and how to restore their function in cases where there is a lack of Tregs or if the Tregs do not function properly. This invention provides a solution to overcome such Treg deficiency and/or Treg dysfunction. In the examples herein it is shown that inosine administration or the administration of a bacterial strain that can stimulate the production of inosine can result in prolonged survival and other beneficial effects in SF mice, thereby apparently compensating for Treg deficiency/dysfunction in such mice.

The term "decrease" or "reduce" or "deficiency" (or equivalent terms) as described herein, e.g. in relation to levels of survival, cytokines, TH1 cells, TH2 cells or Tregs, includes any measurable decrease or reduction when compared with an appropriate control. Appropriate controls would readily be identified by a person skilled in the art and might include non-treated subjects or a level of a particular parameter in the same individual subject measured at an earlier time point (e.g. comparison with a "baseline" level in that subject). Preferably the decrease or reduction will be significant, for example clinically or statistically significant.

The term "increase" or "enhance" (or equivalent terms) as described herein, e.g. in relation to levels of survival, cytokines, TH1 cells, TH2 cells or Tregs, includes any measurable increase or elevation when compared with an appropriate control. Appropriate controls would readily be identified by a person skilled in the art and might include non-treated subjects or a level of a particular parameter in the same individual subject measured at an earlier time point (e.g. comparison with a "baseline" level in that subject). Preferably the increase will be significant, for example clinically or statistically significant.

Methods of determining the statistical significance of differences between test groups of subjects or differences in levels of a particular parameter are well known and documented in the art. For example herein a decrease or increase in level of a particular parameter or a difference between test groups of subjects is generally regarded as statistically significant if a statistical comparison using a significance test shows a probability value of <0.05. Some appropriate statistical methods are outlined below in the Examples.

The invention will be further described with reference to the following non-limiting Examples:

EXAMPLES

TABLE 1

Antibodies and cytokines used

| Antibody/ Cytokine Name | Target Antigen | Vendor | Cat # | Proper Citation | Clone ID | Assay and species | Validation |
| --- | --- | --- | --- | --- | --- | --- | --- |
| LEAF Purified anti-mouse CD3ε | CD3ε | BioLegend | 100314 | (BioLegend Cat# 100314, RRID: AB_312679) | 145-2C11 | Activ, mouse | AntibodyRegistry |
| LEAF Purified anti-mouse CD28 | D28 | BioLegend | 102112 | (BioLegend Cat#102112, RRID: AB_312877) | 37.51 | Costim, mouse | AntibodyRegistry |
| LEAF Purified anti-mouse IL-4 | IL-4 | BioLegend | 504108 | (BioLegend Cat# 504108, RRID: AB_315322) | 11B11 | Neut, mouse | AntibodyRegistry |
| LEAF Purified anti-mouse IFNγ | IFN-γ | BioLegend | 505812 | (BioLegend Cat# 505812, RRID: AB_315406) | XMG1.2 | Neut, mouse | AntibodyRegistry |
| FITC anti-mouse/ human CD44 | CD44 | BioLegend | 103006 | (BioLegend Cat# 103006, RRID: AB_312957) | IM7 | FC, mouse, human | AntibodyRegistry |
| PE anti-mouse CD45RB | CD45RB | BioLegend | 103308 | (BioLegend Cat# 103308, RRID: AB_313015) | C363-16A | FC, mouse | AntibodyRegistry |
| PerCP/Cy5.5 anti-mouse CD4 | CD4 | BioLegend | 100434 | (BioLegend Cat# 100434, RRID: AB_893324) | GK1, 5 | FC, mouse | AntibodyRegistry |
| APC anti-mouse CD62L | CD62L | BioLegend | 104412 | (BioLegend Cat# 104412, RRID: AB_313099) | MEL-14 | FC, mouse | AntibodyRegistry |
| Alexa Fluor 488 anti-mouse IFN | IFN-γ | BioLegend | 505813 | (BioLegend Cat# 505813, RRID: AB_493312) | XMG1.2 | FC, mouse | AntibodyRegistry |

TABLE 1-continued

Antibodies and cytokines used

| Antibody/ Cytokine Name | Target Antigen | Vendor | Cat # | Proper Citation | Clone ID | Assay and species | Validation |
|---|---|---|---|---|---|---|---|
| PE anti-mouse IL-4 | IL-4 | BioLegend | 504104 | (BioLegend Cat# 504104, RRID: AB_315318) | 11B11 | FC, mouse | AntibodyRegistry |
| Recombinant Mouse IL-4 | | BioLegend | 574306 | Accession# NM_021283 | | Activ, mouse | |
| Recombinant Mouse IL-12 | | R&D | 419-ML | Accession # P43432, Accession # NP_032377 | | Activ, mouse | |
| Recombinant Mouse IL-2 | | R&D | 402-ML | Accession # P04351 | | Activ, mouse | |

TABLE 2

Sequences of qPCR primers used

| Gene Name | Forward Primer | Reverse Primer |
|---|---|---|
| mGapdh | AACTTTGGCATTGTGGAAGG | GGATGCAGGGATGATGTTCT |
| mIFNγ | GCGTCATTGAATCACACCTG | GAGCTCATTGAATGCTTGGC |
| mIL-4 | TCTCGAATGTACCAGGAGCC | GGTGTTCTTCGTTGCTGTGA |
| mENT1 | CAGCCTCAGGACAGGTATAAGG | GTTTGTGAAATACTTGGTTGCGG |
| mCNT2 | TTCACGAAGGCGAGAAGTTT | CCAAAGATTCAGGTGGGTGT |

Methods

Mice

Wild-type C57BL/6 and heterozygous B6.Cg-Foxp3sf/J female mice were purchased from Jackson Laboratories. All mice were then bred and housed at The University of Texas Health Science Center at Houston, Houston, Tex., USA under institutionally-approved protocols (Institutional Animal Care and Use Committee no. AWC-14-056). Heterozygous B6.Cg-Foxp3sf/J female mice were bred to C57BL/6J male mice to generate hemizygous B6.Cg-Foxp3sf/Y, scurfy (SF) male mice. Because the Foxp3 gene is on the X chromosome, in each litter of breeding pairs, all males are either SF used as the experiments or WT littermates as the controls.

Animal numbers used in each group of different experiments are indicated in the Figures and Figure Legends.

L. reuteri Preparation and Treatment of SF Mice

Figure 1:
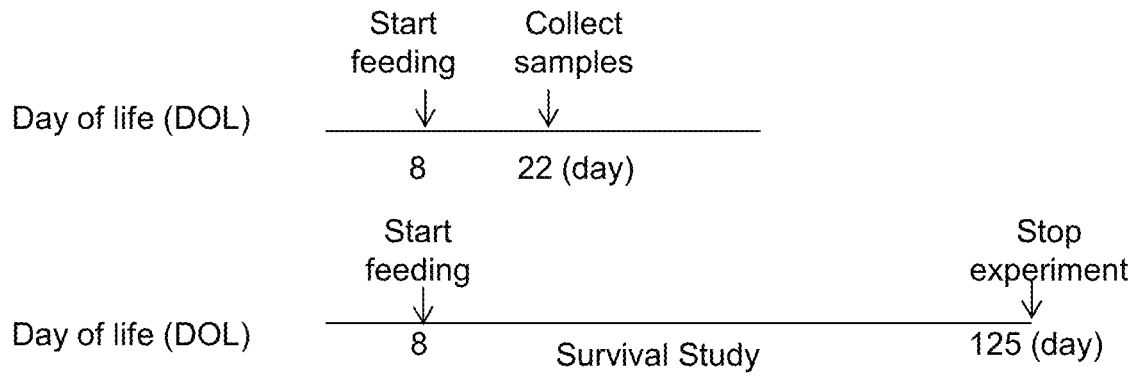
FIG. 1: Experimental scheme. a, Scheme for *L. reuteri* early treatment of SF mice (SFL), starting at 8 days of age (d8), daily, to d125 for survival determination. b, *L. reuteri*: late treatment of SF mice (SFL), starting at d15, daily, to d38 for survival determination. c, Inosine treatment of SF mice (SFI), starting on d8, given daily until d125 for survival analysis.
Figure 1:
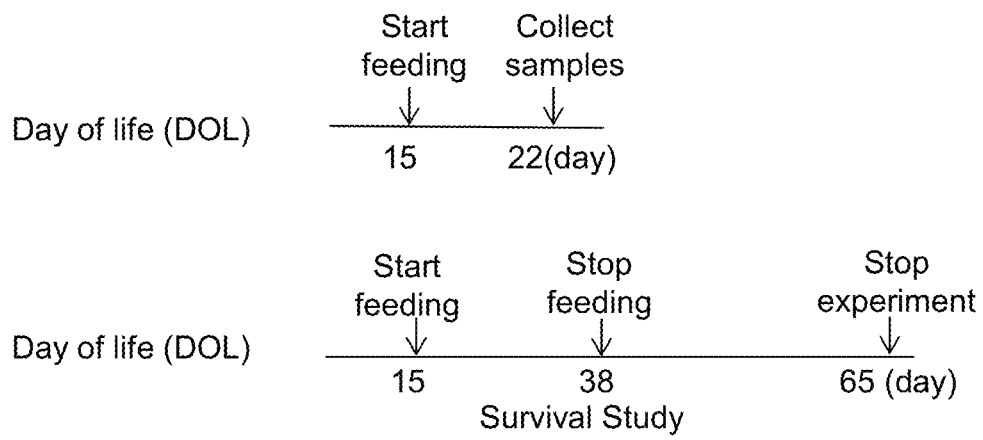
Figure 1:
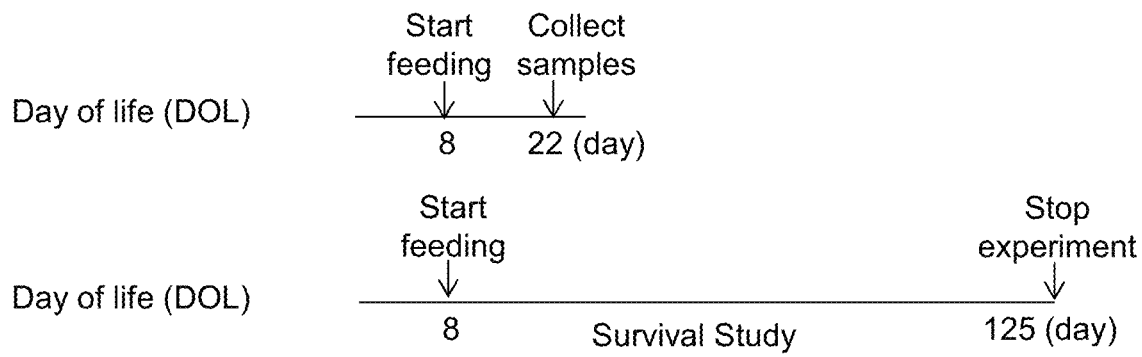

Human breast milk-derived *Lactobacillus reuteri* DSM17938 (*L. reuteri*) was provided by Biogaia AB (Stockholm, Sweden). *L. reuteri* was prepared as described previously (Liu Y. et al. Am. J. Physiol Gastrointest. Liver Physiol 307, G177-G186 (2014)). SF mice were given *L. reuteri* by gavage, daily, starting from 8 days of life (d8) (*L. reuteri* early treatment) or d15 (*L. reuteri* late treatment), until the end of the experimental procedure, as indicated in the FIG. 1a and b, respectively. Each mouse was given $10^7$ CFU of *L. reuteri* per day. Since SF mice generally demonstrate SF phenotype on d13-d15, all male mice were fed *L. reuteri* for early treatment. After daily observation, only male mice that eventually demonstrated SF phenotype and confirmed Foxp3-negative T cells in splenocytes by flow cytometry were labeled as SF+*L. reuteri* (SFL).

Inosine Preparation and Treatment of SF Mice

Inosine (Sigma-Aldrich) was dissolved in sterilized water at 40 mg/ml. For determining the effect of inosine on autoimmunity in SF mice, 800 mg/kg of inosine per day was orally administered to SF mice from d8 until the end of the experiment, as indicated in FIG. 1c.

Histopathology

All tissues obtained from WT and SF mice (FIG. 1), were fixed and processed by the Cellular and Molecular Morphology Core Lab (the Texas Medical Center Digestive Diseases Center, Houston, Tex.) and stained with hematoxylin and eosin (H&E) for histological evaluation. The area of lymphocyte infiltration of liver and lung and the villus height and crypt depth of small intestine were measured using Image J morphometry software (NIH, USA).

In Vitro Tissue Preparation and Stimulation for Flow Cytometry Analysis

Single cell suspensions from the spleen and mesenteric lymph nodes (MLN) were obtained by gently fragmenting and filtering the tissues through 40 μm cell strainers (BD Bioscience) into MACS buffer consisting of phosphate buffered saline (PBS), 0.5% bovine serum albumin (BSA) (Hyclone Laboratories) and 2 mM EDTA (Lonza).

For in vitro stimulation, cells were stimulated with phorbol 12-myristate 13-acetate (PMA) (50 ng/mL) and ionomycin (1 μg/mL) in the presence of brefeldin A (5 μ/mL) for 4 hours to analyze IFN-γ-producing (TH1) and IL-4-producing (TH2) CD4+ T cells.

Naïve CD4+ T Cell Isolation and In Vitro Differentiation to TH1 and TH2

Naïve CD4+ T cells were isolated from the spleens of 6-8-week-old C57BL/6 or adenosine receptor knockout mice by magnetic cell sorting, using a naïve CD4+ T cell isolation kit (MACS Miltenyi Biotec).

For TH1 differentiation, naïve T cells ($5 \times 10^5$ cells/well) were plated in 24-well plates containing 1 μg/mL anti-CD3, 2 μg/mL anti-CD28, 20 ng/mL IL-2, 10 μg/mL anti-IL-4 neutralizing antibody, and 20 ng/mL recombinant mouse IL-12 in RPMI1640 complete medium at 37° C. for 5 days with or without 2 mM of inosine.

For TH2 differentiation, naïve T cells were cultured in the presence of 1 μg/mL anti-CD3, 2 μg/mL anti-CD28, 20 ng/mL 11-2, 10 μg/mL anti-IFN-γ neutralizing antibody and 10 ng/mL recombinant mouse IL-4 in RPMI1640 complete medium at 37° C. for 5 days with or without 2 mM of inosine. At day 5, the cells were stimulated with PMA and inomycin in the presence of brefeldin A, as mentioned above.

The detailed antibodies and cytokines used are listed in Table 1.

Staining Cells for Flow Cytometry Analysis

For evaluation of the purity of naïve CD4+ T cells, after sorting, cells were stained using fluorescein-labeled CD44, CD45RB, CD4, and CD62L.

For characterization of TH1 and TH2 cells, cells were surface-stained by fluorescein-labeled-CD4 and intracellularly stained with IFN-γ for TH1 and IL-4 for TH2. Intracellular staining was performed with a fixation/permeabilization kit, according to the manufacturer's protocol (eBioscience, San Diego, Calif.).

The data from all samples were acquired on BD FACSCalibur and analyzed by using FlowJo software (Tree-Star, Inc. Ashland, Oreg.).

The detailed antibodies used are listed in Table 1.

Lymphocyte Proliferation Test

Splenic lymphocytes were split into 96-well plates at an initial density of $2\times10^4$ cells per well and were incubated with different doses of inosine under control, 40 μg/ml of LPS or 10 μg/ml of PHA condition, respectively. After 96 h, cell viability was measured by TACS XTT cell proliferation assay kit (Trevigen, Inc. Gaithersburg, Md.).

Plasma Cytokine Assays

Plasma cytokine levels of IFN-γ, IL-4, IL-2, IL-1β and IL-10 were assessed using a mouse multi-spot proinflammatory panel kit from Meso Scale Discovery (Gaithersburg, Md.), according to the manufacturer's protocol.

Stool Microbial Community Analysis

Feces expressed from cecum to rectum were collected from groups of WT, SF and SF with L. reuteri treatment (SFL) at the indicated age (FIG. 1a-b). Stool DNA was extracted by using Quick Stool DNA Isolation Kit (Qiagen). The composition of the stool microbiota was analyzed using high-throughput sequencing analysis of PCR-amplified 16s rRNA genes as previous described (Gupta, R. W. et al. J. Pediatr. Gastroenterol. Nutr. 56, 397-400 (2013)). Bacterial diversity, species composition and abundance were assessed using QIIME (Caporaso, J. G. et al. Nat. Methods 7, 335-336 (2010)).

Plasma and Stool Metabolomic Analysis

Plasma and stool metabolites were measured by Metabolon Inc as previous described (He B. et al. Sci. Rep. 5, 10604 (2015)). A total of 657 metabolites in stool and 525 metabolites in plasma were detected by a non-targeted metabolomic analysis platform including UPLC-MS/MS and GC/MS, respectively. The metabolomic data were then analyzed by pattern recognition analyses (unsupervised principal component analysis and Heat-map), revealing the biochemical perturbations induced by Treg-deficiency or L. reuteri treatment.

Statistical Analysis

Figure 2:
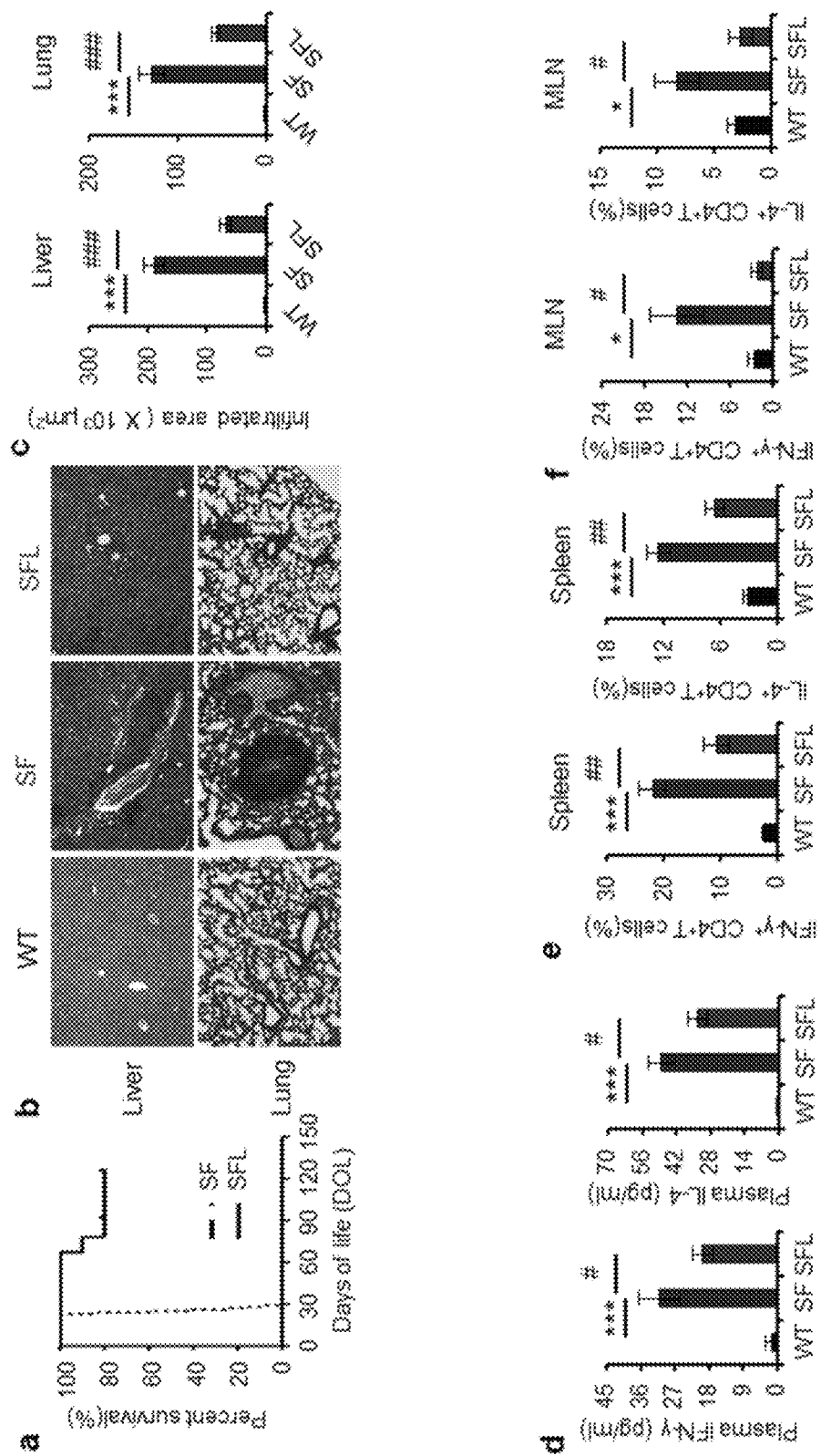
FIG. 2: *L. reuteri* treatment early in life increases survival and suppresses autoimmunity in SF mice. a, Survival curves of SF (n=17) and SFL (LR-treated beginning on d8)(n=10) mice. b, Representative H&E staining of liver and lung of WT, SF and SFL mice at d22. c, Quantitation by morphometry of inflammatory infiltrates in liver and lung of WT (n=12), SF (n=12) and SFL (n=10). d, Levels of IFN-γ and IL-4 in plasma. e, f, The proportion of IFN-γ or IL-4- producing-CD4$^+$T cells in spleen (e) and mesenteric lymph nodes (f). Error bars, means±s.e.m. *p<0.05, ***p<0.001. SF vs. WT. #p<0.05, ##p<0.01, ###p<0.001. SFL vs. SF.

All replicates in this study were biological; that is, repeat experiments with additional mice. D'Agostino-Pearson omnibus test was used to verify that all data were normally distributed. Significance was determined using one-way ANOVA corrected for multiple comparisons with Tukey and Dunnett's posttests, or two-way ANOVA for multiple comparisons with a Bonferroni test. Data are presented as mean±s.e.m. Kaplan-Meier survival curves were graphed, and the comparison was analyzed using Logrank with Chi-square test. The statistical analysis was performed using GraphPad Prism version 4.0 (GraphPad Software, San Diego, Calif., USA). Differences were noted as significant at $P<0.05$. No statistical methods were used to predetermine sample size. There were no animals excluded from analysis. No randomization was used. All histological analyses were done by 2 blinded observers (FIGS. 1, 2, and 4. FIGS. 6, 8, 9, and 14).

Example 1

L. reuteri Treatment in T-Reg Deficient Mice

To determine whether targeting gut microbiota could impact Treg deficiency-associated autoimmunity, we treated SF mice with the human commensal L. reuteri DSM 17938, beginning at 8 days ("early") or 15 days ("late") of age (FIG. 1a, b) according to the method described above. Either early or late treatment significantly prolonged the survival of SF mice (FIG. 2a and FIG. 3a). In addition, L. reuteri reduced inflammatory infiltration in liver and lung (FIG. 2b, c and FIG. 3b, c). The level of cytokines IFN-γ and IL-4 in plasma, and the frequencies of TH1 and TH2 cells in the spleen and MLN were reduced by L. reuteri (FIG. 2d-f and FIG. 3d, e). L. reuteri also rescued the effects of Treg-deficiency on villus height and crypt depth in the small intestine (FIG. 4a-c). The histopathology, cytokine measurements and lymphocyte investigation were done as described above. These results show that L. reuteri may treat, as well as prevent, autoimmunity in SF mice, and also that L. reuteri can be used in the treatment of a T-reg deficient disease such as IPEX in humans.

Example 2

Metabolomic Profile

Given that metabolites of commensal bacterial metabolism play a key role in microbe-host interaction, we analyzed metabolomic profiles of feces and plasma, according to the methods described above. 657 and 525 metabolites in feces and plasma, respectively (FIG. 5a, c and Table 1, 2). Treg-deficiency led to significant alterations in 11% and 51% of all detected metabolites in feces and plasma, respectively (FIG. 5b, d and Table 1, 2). Interestingly, L. reuteri treatment had a significant impact on the fecal and plasma metabolome associated with Treg-deficiency (FIG. 5a-d).

When we focused on plasma metabolites that were significantly altered by Treg-deficiency and restored to control levels by L. reuteri, we observed that inosine was decreased a 5-fold in SF, but was completely restored by L. reuteri treatment (FIG. 6, FIG. 5e and Table 2). Other metabolites involved in inosine metabolism were altered in plasma by Treg-deficiency but not restored by L. reuteri treatment (FIG. 7a).

Notably, the level of inosine in feces was not changed by Treg-deficiency but was reduced by L. reuteri treatment (FIG. 6). The reduced inosine in feces might be related to the increased absorption in the small intestine, due to improvement of villus height, crypt depth in the intestine. Other metabolites involved in inosine metabolism were unchanged in feces of SFL mice (FIG. 7b).

Example 3

Oral Treatment of Inosine in T-Reg Deficient Mice

We examined whether increasing plasma inosine was sufficient to suppress Treg deficiency-mediated autoimmunity according to the methods and analysis as described above. Oral feeding inosine to SF mice significantly prolonged their survival (FIG. 8a and FIG. 1c). Inosine also reduced the inflammatory cell infiltration of liver and lung, the levels of cytokines IFN-γ and IL-4 in plasma, and the frequency of TH1 and TH2 cells in the spleen (FIG. 8c-f). In addition, inosine inhibited differentiation of TH1 and TH2 cells (FIG. 8b and FIG. 9d, e), but did not inhibit the proliferation of lymphocytes in vitro (FIG. 9a-c). The histopathology, cytokine measurement and lymphocyte investigation were done as described above. These findings show that the effect of inosine in SF mice may due to inhibition of TH1/TH2 cell differentiation. On the basis of these results, inosine can be used in the treatment of a T-reg deficient disease such as IPEX in humans.

The invention claimed is:

1. An in vivo method for selecting a lactic acid bacterial strain capable of stimulating inosine production, wherein the method comprises detecting or determining the amount or level of inosine stimulation by a bacterial strain by:
   a) administering a bacterial strain to a suitable animal model;
   b) obtaining samples from the animal model;
   c) measuring the levels of inosine in the sample;
   and selecting a bacterial strain which has the ability to stimulate inosine production in vivo.

2. The method of claim 1, wherein the animal model is an experimental mouse model system.

3. The method of claim 1, wherein the selected strain is *Lactobacillus reuteri*.

4. The method of claim 1, further comprising culturing or propagating or producing the bacterial strain.

5. The method of claim 1, wherein the sample is a systemic sample or a stool or GI tract sample.

6. The method of claim 5, wherein the systemic sample is a plasma, blood, or serum sample.

7. The method of claim 1, wherein the method comprises measuring the levels of inosine without administration of the bacterial strain and comparing the levels of inosine in step (c) to the levels observed in the absence of the strain.

8. The method of claim 1, wherein the selected strain is not *Lactobacillus reuteri* DSM 17938.

9. The method of claim 1, wherein the experimental mouse model system is a scurfy mouse model.

10. The method of claim 7, wherein the experimental mouse model system is a scurfy mouse model.

11. The method of claim 7, wherein the selected strain is not *Lactobacillus reuteri* DSM 17938.

12. The method of claim 1, further comprising lyophilizing or freeze drying the bacterial strain.

* * * * *